United States Patent
Blum et al.

(10) Patent No.: US 6,207,290 B1
(45) Date of Patent: Mar. 27, 2001

(54) ANTIFOULANT COMPOSITIONS AND METHODS OF TREATING WOOD

(75) Inventors: Melvin Blum, Wantagh, NY (US); Michael Roitberg, Highland Park, NJ (US)

(73) Assignee: Burlington Bio-Medical & Scientific Corp., Farmingdale, NY (US)

( * ) Notice: Subject to any disclaimer, the term of this patent is extended or adjusted under 35 U.S.C. 154(b) by 0 days.

(21) Appl. No.: 09/055,785

(22) Filed: Apr. 7, 1998

(51) Int. Cl.[7] .................................. B05D 3/00; B32B 7/00
(52) U.S. Cl. ........................ 428/540; 428/195; 428/541; 428/543; 106/18.32; 106/18.28
(58) Field of Search ..................................... 428/540, 541, 428/195, 543; 106/18.32, 18.28

(56) References Cited

U.S. PATENT DOCUMENTS

| | | |
|---|---|---|
| 3,896,753 | 7/1975 | Shepherd et al. . |
| 3,981,252 | 9/1976 | Ticker . |
| 3,990,381 | 11/1976 | Shepherd et al. . |
| 4,168,562 | 9/1979 | Maasberg . |
| 4,624,679 | 11/1986 | McEntee . |
| 4,761,247 | 8/1988 | Rei et al. . |
| 4,842,932 | 6/1989 | Burton . |
| 4,891,391 | 1/1990 | McEntee . |
| 4,995,914 | 2/1991 | Teter . |
| 5,118,346 * | 6/1992 | Wehner et al. ...................... 106/18.3 |
| 5,167,721 | 12/1992 | McComas et al. . |
| 5,376,705 | 12/1994 | Leys et al. . |
| 5,397,385 | 3/1995 | Watts . |
| 5,466,299 | 11/1995 | Jan . |
| 5,603,775 | 2/1997 | Sjoberg . |
| 5,628,271 | 5/1997 | McGuire . |
| 5,629,045 | 5/1997 | Veech . |
| 5,635,192 | 6/1997 | Terry et al. . |
| 5,639,464 | 6/1997 | Terry et al. . |

FOREIGN PATENT DOCUMENTS

| | | |
|---|---|---|
| 0 745 325 | 12/1996 | (EP) . |
| 53-28632 * | 3/1978 | (JP) ............................... C09D/3/58 |
| 2-18468 | 1/1990 | (JP) . |
| 3-90005 | 4/1991 | (JP) . |

OTHER PUBLICATIONS

Chemical Abstract vol. 72:80438y (1970).
Chemical Abstracts vol. 81:65344g (1974).
Chemical Abstract vol. 67:22923p (1967).
Chemical Abstracts vol. 82:32508f (1975).
Chemical Abstracts vol. 85:889b (1976).
Chemical Abstracts vol. 85:890v (1976).

* cited by examiner

Primary Examiner—William Krynski
Assistant Examiner—Dawn L. Garrett
(74) Attorney, Agent, or Firm—Oliff & Berridge, PLC

(57) ABSTRACT

Antifoulant compositions include 10,10'-oxybisphenoxarsine and/or phenarsazine oxide with a quaternary ammonium salt. The antifoulant compositions may also include adjuvants such as fungicides, ultraviolet absorbers, and antioxidants. The antifoulant compositions can be used in fresh or sea water paints. In addition, the antifoulant composition may be used to stain or impregnate wood, thus preserving the wood.

26 Claims, 1 Drawing Sheet

ANTIFOULANT COMPOSITIONS AND METHODS OF TREATING WOOD

BACKGROUND OF THE INVENTION

1. Field of Invention

Figure 1:
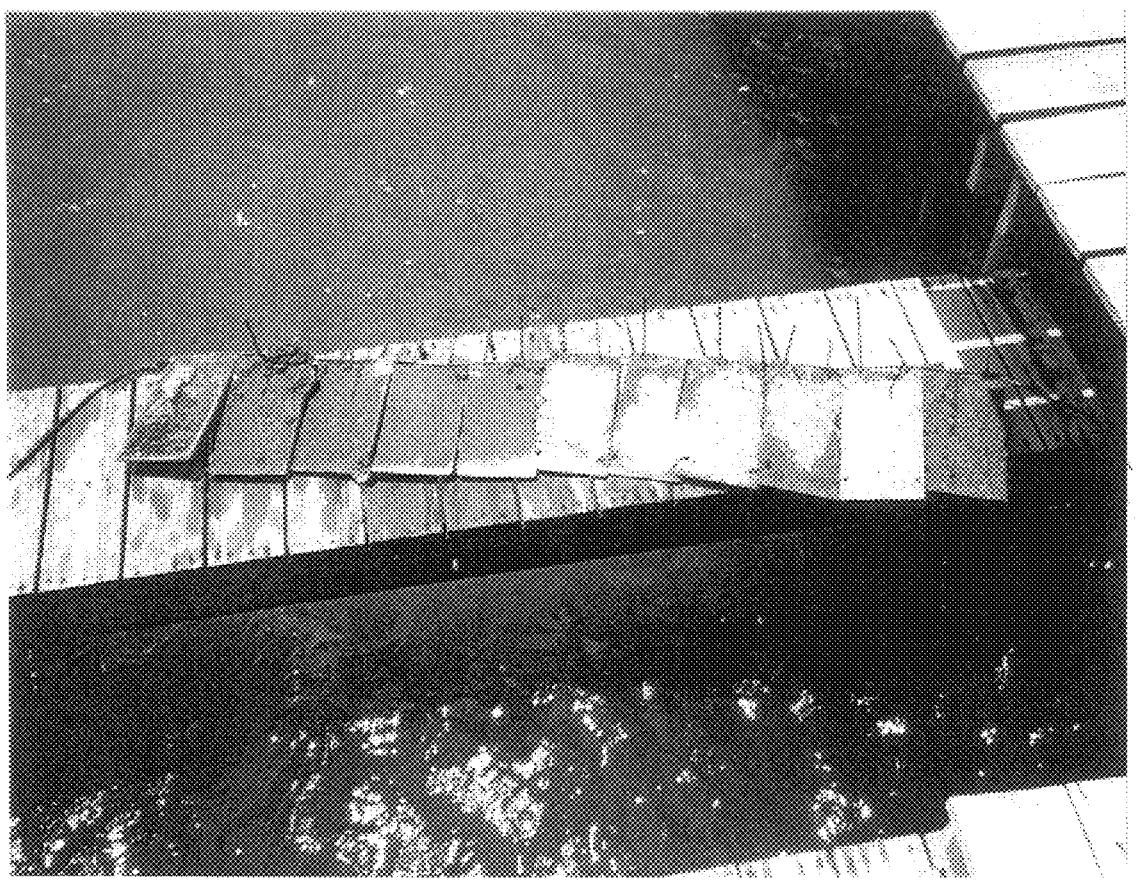

The present invention is directed to antifoulant compositions and methods of treating wood with such compositions. More specifically, the present invention is directed towards fresh and sea water antifoulant compositions comprising 10,10'-oxybisphenoxarsine (OBPA) and/or phenarsazine oxide (PZO) with a quaternary ammonium salt.

2. Description of Related Art

Antifoulant compositions containing OBPA or PZO are generally known.

U.S. Pat. Nos. 3,990,381 and 3,896,753 to Shepherd et al. disclose hydrophilic polymers having encapsulated therein antifouling agents that are applied as a coating to underwater portions of a marine structure. The inorganic and organic antifoulants include cuprous oxide and 10,10'-oxybisphenoxarsine.

JP 02-18468 A1 discloses a coating containing 10,10'-oxybisphenoxarsine to prevent aquatic organisms and algae from sticking to materials such as fishing nets.

USSR 248,121 (CAS 72:80438y) discloses antifoulant paints consisting of an arsenic compound such as bis(phenoxarsin-10-yl)ether. USSR 248,121 (CAS 81:65344g) discloses antifoulant paints prepared by mixing pigments and phenoxarsine derivatives such as bis(10-phenoxarsyl) oxide.

Chemical Abstract vol. 67:22923p discloses an organotoxic antifouling paint containing phenarsazine derivatives such as phenarsazine oxide.

U.S. Pat. No. 5,397,385 to Watts discloses an antifouling coating composition that uses capsaicin as an antifouling agent. The antifouling composition can be used in combination with conventional antifouling coatings, paints and binders and applied to wood, metal and plastic surfaces. The antifouling composition may also be added to other materials in molding processes to form various articles of manufacture and molded products, such as boat hulls and water pipes, to resist fouling by organisms common in fresh water and sea water.

U.S. Pat. No. 5,629,045 to Veech discloses coatings containing lipid soluble, non-toxic biodegradable substances that prevent fouling of marine structures such as boats by shell bearing sea animals, such as barnacles. A preferred inhibitor is pepper containing capsaicin. The inhibitor is incorporated into standard marine paints, impregnants, varnishes and the like.

JP 03 90005 discloses making a rubber composition containing OBPA into a sheet to prevent shellfish from adhering to ships.

U.S. Pat. Nos. 5,639,464 and 5,635,192 to Terry et al. disclose biocidal protective coatings for heat exchanger coils formed by applying a polymeric composition containing an organic water resistant polymer that has associated with it an effective amount of a biocidal compound to inhibit corrosion, fouling, and biocidal buildup on the coils. The biocidal compounds may be 10,10-oxybisphenarsine.

U.S. Pat. No. 5,367,705 to Leys et al. discloses a waterproof coating that is virtually ingestion proof by marine life and that may contain denatonium saccharide, synthetic capsaicin and an ultraviolet absorber.

SUMMARY OF THE INVENTION

The present invention is directed to marine antifoulant compositions comprising 10,10'-oxybisphenoxarsine (OBPA) and/or phenarsazine oxide (PZO) with quaternary ammonium salts. In embodiments, the antifoulant compositions may further comprise fungicides, ultraviolet absorbers, and antioxidants. The compositions can be used, for example, in fresh or sea water antifoulant paints. In addition, the compositions can be used, as solutions or stains, to impregnate wood, for example, bulkheads, piers, docks, foundations, rail ties, posts, pilings, groins, construction timber, and the like.

The compositions according to the present invention exhibit superior and unexpected results with respect to biocidal lifetime as compared to traditional compositions. In addition, the organic arsenic compounds of the present invention are much less toxic to the environment than traditional copper, chromium, and arsenic (CCA) based preservatives since they do not leech out. Further, OBPA and PZO are not affected by electrolytic degradation such as the copper, tin and zinc salts in conventional antifoulants. Moreover, the composition according to the present invention are much lighter than conventional antifoulant compositions containing toxic or heavy metal compounds or their salts and oxides.

DETAILED DESCRIPTION OF PREFERRED EMBODIMENTS

According to the present invention, an antifoulant composition comprises OBPA and/or PZO and a quaternary ammonium salt. In embodiments, other organo arsenicals can be used in place of, or in combination with, OBPA and/or PZO, including, but not limited to, arsanilic acid, roxarsone, methyl arsonic acid, mono methyl arsinic acid, mono sodium methyl arsonate (MSMA), and cacodylic acid. The antifoulant compositions contain any effective amount of OBPA and/or PZO. In embodiments the antifoulant compositions contain about 0.5–50 wt. % of an organo arsenical, preferably about 2–25 wt. %, and more preferably about 3–7 wt. % of the composition.

According to the present invention, a quaternary ammonium salt may be added to the antifoulant compositions as a stabilizer and synergizer. The quaternary ammonium salts include, but are not limited to, denatonium saccharide, denatonium chloride, denatonium benzoate, denatonium oleate, palmitate, lidocaine, lidocaine HCl, benzylalkonium salts and combinations thereof. In embodiments, the quaternary ammonium salts are added in an amount of about 0.05–10 wt. %, more preferably about 1–3 wt. % of the composition.

In embodiments, the composition may optionally contain about 0.2 to about 20 wt. % capsaicinates, preferably about 0.5 to about 5 wt. % denatonium capsaicinate. Other compositions are exemplified by U.S. Patent Application Serial No. 08/929,621, incorporated by reference herein in its entirety.

The antifoulant compositions according to the present invention work exceptionally well as antifoulant additives for fresh and sea water antifoulant paints. Further, if OBPA and/or PZO solutions are soaked or impregnated into wood, the resultant treated wood is as good as conventional CCA (Copper, Chromium and Arsenic) pressure treated wood that is conventionally used for protecting bulk heads, piers, docks, ties, posts, piling, construction timber, and the like. Solvents used to treat or impregnate wood with the compositions of the present invention include, but are not limited to, isodecyl alcohol (IDA), benzyl alcohol, methanol, dimethyl sulfoxide, hexane diol, chloroform, phentyl alcohol, propylene glycol, 3-phenyl 1-propanol, methylene chloride, nonyl phenol, benzene, triphenyl phosphate, toluene, benzaldehyde, dimethyl formamide, isopropyl alcohol, ethyl cellusolve, methyl cellusolve, dioctyl phthalate. CCA normally comprises 25 wt. % arsenic acid, 25 wt. % chromic acid, 15 wt. % cupric oxide, and water (balance).

One advantage of the antifoulant compositions of the present invention is that OBPA and PZO are organoarsenicals. Thus, the antifoulants are far less toxic than inorganic arsenic compounds. In addition, the antifoulant, biocidal, insecticidal, and fungicidal compositions of the present inventions, being mostly insoluble, do not leach into the water as much as inorganic arsenicals; therefore, they do not pose as serious an environmental hazard as CCA and other soluble arsenates and arsenites. In fact, certain aquatic organisms actually contain large quantities of organically bound arsenic that humans ingest with no ill effects. OBPA is only water soluble up to about 5 ppm in fresh water, and is less soluble in sea water.

Another advantage of the antifoulant compositions of the present invention is that, unlike conventional antifoulants (e.g., copper oxide, tributyl tins, zinc pyrithione, copper omadine, and the like), OBPA and PZO are not affected by the electrolytic degradation of copper, tin and zinc. Apparatuses that are most susceptible to galvanic action include rudders, propellers, shafts, stem frames, depth finders, outdrives, transmissions, buoys, and the like. Therefore, in embodiments, the antifoulant compositions of the present invention last much longer and work more effectively in paints and adhere better on matrices to which they are applied. In embodiments, matrices used to encapsulate the antifoulant compositions of the present invention include, but are not limited to, polyvinyl, polyurethane, acrylic, Teflon, epoxy coatings, and the like. In embodiments, the antifoulant composition is melted and blended with the matrix polymer. In additional embodiments, the antifoulant composition may be in pellet form and subsequently crushed or pulverized or mixed with the matrix polymer to form a powder which is then added to a paint.

The paint compositions of the present invention are also much lighter (e.g., about 50–75 wt. %) than conventional copper based antifoulant paints. In addition, wood treated with the antifoulant compositions of the present invention are much lighter (e.g., 80–99 wt. %) lighter than CCA impregnated wood. Known antifoulant paints usually require large quantities of metal-containing antifoulant compositions (e.g., 30 wt. %–75 wt. % of the paint) in order to be effective. Thus, conventional antifoulant paints are (1) very heavy, particularly when considering a copper oxide based antifoulant; (2) highly active from an electrolysis standpoint; (3) more costly due to the larger quantities of active ingredients needed; and (4) are more toxic from an ecological standpoint. For example, a gallon of copper based paints can weigh from about 16–33 lbs., depending on the cuprous oxide content. In contrast, a gallon of OBPA antifoulant paint can weight about 8.5–10.5 lbs., depending on the matrix used. Further, when OBPA is added to a conventional cuprous oxide antifoulant paint, the actual level of cuprous oxide can be cut in half even when using only about 0.5 wt. % to about 1 wt. % OBPA. If 3 wt. % or more OBPA or PZO are used in the paint formula, no other metallic antifoulants may be necessary. Further, OBPA and PZO do not affect paint rheology, color retention, or curing time and do not normally bleed out of the paint when immersed in water.

As noted above, the antifoulant compositions of the present invention have superior antifoulant lifetime. In embodiments, wood impregnated or soaked with the antimicrobial, biocidal, insecticidal, and termiticidal compositions demonstrate a lifetime of about 60 months or greater. Wood treated with the antifoulant, antifungal paints or stains according to the present invention demonstrate a lifetime of 24 months or greater, preferably about 36 months or greater. In contrast, conventional high quality non CCA-based antifoulant, antifungal compositions have an antifoulant, antifungal lifetime of only 6–12 months.

In embodiments, the OBPA/PZO antifoulant compositions may comprise a fungicide including, but not limited to, octyl isothiazalone, 1,2-benzisothiazolin, 5-chloro-2-methyl-4 isothiazolin, 2-methyl-4 isothiazolin, 4,5 dichloro-2-octyl isothiazolin, Triclosan, and combinations thereof. In embodiments, the fungicide may be added in an amount of about 0.05–10 wt. %, more preferably about 1–3 wt. %. The addition of fungicides results in comparable levels of antifoulant protection and substantially reduces the galvanic action that is prevalent with copper, tin and zinc based protective agents and may, in embodiments, lower OBPA and/or PZQ levels.

PZO is more stable to ultraviolet light and it is easier and less costly to produce. When the antifoulant paints are applied at or near the high water levels OBPA is somewhat more light sensitive than PZO, Triclosan or the isothiazalones and is degraded to PAA (phenylarsonic acid). Therefore, in embodiments when ultraviolet stability may be a concern, various ultraviolet absorbers may be added. Ultraviolet absorbers include, but are not limited to, acetaminosalol, benzalphthalide, benzophenones, 3-benzylidine camphor, benzyl salicylate, bis tetramethyl piperidinyl sebacate, bornelone, bumetrizole, butyl methoxydibenzoylmethane, cinoxate, digalloyl trioleate, diisopropyl methyl cinnamate, disodium bisethylphenyl triaminotriazine stilbenedisulfonate, disodium distyrylbiphenyl disulfonate, drometrizole, ethyl diisopropylcinnamate, ethyl methoxycinnamate, ethyl PABA (para amino benzoic acid), ethyl urocanate, etocrylene, ferulic acid, glyceryl octanoate dimethoxycinnamate, glycol salicylate, homosalate, isopropylbenzyl salicylate, isopropyl dibenzoylmethane, menthyl anthranilate, menthyl salicylate, octocrylene, octrizole, octyl salicylate, oxybenzone, octyl triazone, PABA (para amino benzoic acid), phenylbenzimidazole sulfonic acid, piperidine derivatives, polyacrylamidomethyl benzylidene camphor, potassium methoxycinnamate, potassium phenylbenzimidazole sulfonate, sodium phenylbenzimidazole sulfonate, sodium urocanate, terephthalyidene dicamphor sulfonic acid, titanium dioxide, urocanic acid, VA/Crotonates/Methacryloxybenzophenone-1 copolymer. In embodiments, the ultraviolet absorber is preferably titanium dioxide, oxybenzone, benzophenones, bis tetramethyl piperidinyl sebacate, piperidine derivatives or mixtures thereof.

In embodiments, antioxidants may be added to the antifoulant paint compositions to help prevent OBPA or PZO from oxidizing, thereby extending the compositions' lifetimes by about 20%–200%. Antioxidants include, but are not limited to, high purity non-polymerized ethoxyquin, ethoxyquin phosphate, citrate, maleate, propionate, formate, ascorbic acid, ascorbyl palmitate and dipalmitate, ethyl ascorbate, ascorbyl stearate and oleate, tocopherols and tocotrienols, dodecyl and octyl gallate, gallic acid and tannic acid (including salts and esters thereof), gamma oryzanol, thioctic acid and salts, and combinations thereof. In embodiments, an antioxidant may be added in an amount of about 0.01–10 wt. %, more preferably about 1–3 wt. %.

Unlike conventional antifoulants, the antifoulant compositions of the present invention perform well in water where the temperature ranges from about 40°–90° F., and do not appear to be affected by dirt, oil, brackish water or varying degrees of salinity or pH. The composition may be used on fiberglass, wood, steel, aluminum hulls or underwater bronze parts and work equally well against hard fouling (e.g., barnacles, mussels, balanidae, and the like) and soft fouling (e.g., worms, hydroids, mites, slugs, algae, weeds, flora, fauna, slime, tunicates, and the like).

Preserved wood is usually treated with pentachlorophenol, coal tar, petroleum oil, zinc or copper naphthenate, pyrethroids (synthetic or natural), copper 8-quinolinolate, tetra chlorophenol or chloro 2-phenyl phenol, CCA or creosote. As with such conventional wood treatment, wood treated with the biocidal, insecticidal, and termiticidal compositions of the present invention protect against termites, carpenter ants, carpenter bees and other wood destructive insects, bacteria, fungus, mold, algae, and against marine borers. Further, the biocidal compositions also work as fungicides in textiles, leathers, rubber, and the like.

In order to preserve wood from attack by fungi, insects or borers, it is necessary to apply the OBPA/PZO or admixtures by at least one of the following treatment methodologies: (1) pressure or vacuum treatment, (2) dipping, brushing or spraying, (3) alternating hot and cold thermal baths; and (4) direct injection.

EXAMPLES

Tests conducted over a 36 month period of time have demonstrated the efficacy of antifoulant paint compositions containing OBPA or PZO and denatonium compounds such as denatonium capsaicinate over convention antifoulant paints. Most conventional antifoulant paints work for 3 months to 1 year.

Nine panels were treated with different conventional antifoulant paint compositions containing up to 76 wt. % copper oxide, for example, an ablative formula containing 46 wt. % copper oxide. The conventional paints were obtained from Interlux, Petit Paint and Wolsey Paint companies. One panel was treated with the same conventional paints to which were added about 1 wt. % OBPA and denatonium saccharide, and another panel was treated with 0.75 wt. % OBPA and denatonium capsaicinate, according to the present invention. The panels were placed in sea water for 36 months.

The panels not treated with an antifoulant composition according to the present invention showed significant fouling by marine organisms. In comparison, the two panels treated with antifoulant compositions of the present invention showed little or no fouling by marine organisms. Areas showing fouling were a result of overpainting with conventional paints.

Examples 1–4 below show typical antifoulant paint compositions according to the present invention.

| ANTIFOULANT PAINT FORMULATIONS (wt. %) | |
|---|---|
| Example 1. | |
| Co-polymer A-15 | 16 |
| Rosin | 6 |
| Cuprous oxide | 30 |
| OBPA and Denatonium salts (0.1%) | 2 |
| Chlorinated paraffin | 5 |

| -continued | |
|---|---|
| ANTIFOULANT PAINT FORMULATIONS (wt. %) | |
| Zinc oxide | 3 |
| Solvents (methyl isobutyl ketone, IDA, Cyclohexanone and others) | 28 |
| Titanium dioxide/Silica blend | 10 |
| Example 2. | |
| Perchlorovinyl resin | 16.5 |
| Linseed oil | 3.5 |
| Rosin | 10 |
| Saponite | 24 |
| Zinc oxide | 5 |
| OBPA and Denatonium salts (0.1%) | 3 |
| Titanium oxide/Silica blend | 6 |
| Solvents (acetone, solvent-naphtha, IDA, Butyl acetate, cyclohexanone) | 32 |
| Example 3. | |
| Acrylic/polyamide resins | 30 |
| Linseed oil | 3 |
| Rosin | 3 |
| Saponite | 22 |
| Titanium dioxide | 8 |
| PZO and Denatonium salts (0.1%) | 2 |
| Solvents (methyl isobutyl ketone, IDA, Cyclohexanone and others) | 32 |
| Example 4. | |
| Perchlorovinyl resin | 3.3 |
| Rosin | 6.6 |
| Cuprous oxide | 34.1 |
| Zinc oxide | 5 |
| PZO and Denatonium salts (0.1%) | 3 |
| Solvents (acetone, solvent-naphtha, IDA, Butyl acetate, cyclohexanone) | 32 |
| Dibutyl phthalate | 2 |
| Saponite | 14 |

What is claimed is:

1. An antifoulant composition comprising:
   a quaternary ammonium salt;
   a compound selected from the group consisting of 10,10'-oxybisphenoxarsine, phenarsazine oxide, arsanilic acid, roxarsone, methyl arsonic acid, mono methyl arsinic acid, mono sodium methyl arsonate, cacodylic acid and combinations thereof; and
   an ultraviolet absorber.

2. The antifoulant composition of claim 1, wherein said quaternary ammonium salt is denatonium capsaicinate.

3. The antifoulant composition of claim 1, wherein said compound is present in an amount of about 0.5 to about 50 wt. % of the composition.

4. The antifoulant composition of claim 2, wherein said denatonium capsaicinate is present in an amount of about 0.5 to about 5 wt. % of the composition.

5. The antifoulant composition of claim 1, wherein said quaternary ammonium salt is selected from the group consisting of denatonium saccharide, denatonium chloride, denatonium benzoate, denatonium oleate, palmitate, lidocaine, lidocaine HCl, benzylalkonium salts and combinations thereof.

6. The antifoulant composition of claim 1, further comprising a fungicide.

7. The antifoulant composition of claim 6, wherein said fungicide is selected from the group consisting of octyl isothiazalone, 1,2-benzisothiazolin, 5-chloro-2-methyl-4 isothiazolin, 2-methyl-4 isothiazolin, 4,5 dichloro-2-octyl isothiazolin, Triclosan, and combinations thereof.

8. The antifoulant composition of claim 6, wherein said fungicide is present in an amount of about 0.05–10 wt. % of the composition.

9. The antifoulant composition of claim 1, further comprising an antioxidant.

10. The antifoulant composition of claim 9, wherein said antioxidant is selected from the group consisting of ethoxyquin, ethoxyquin phosphate, citrate, maleate, propionate, formate, ascorbic acid, ascorbyl palmitate and dipalmitate, ethyl ascorbate, ascorbyl stearate and oleate, tocopherols and tocotrienols, dodecyl and octyl gallate, gallic acid and tannic acid, gamma oryzanol, and thioctic.

11. The antifoulant composition of claim 9, wherein said antioxidant is present in an amount of about 0.01–10 wt. % of the composition.

12. The antifoulant composition of claim 1, wherein said ultraviolet absorber is selected from the group consisting of titanium dioxide, oxybenzone, benzophenones, bis tetramethyl piperidinyl sebacate, piperidine derivatives or mixtures thereof.

13. A paint comprising the composition of claim 1.

14. The paint of claim 13, wherein said paint is a fresh water or sea water paint.

15. A method of preserving wood, comprising:
   staining, soaking or impregnating wood with a composition according to claim 1.

16. The method of claim 15, wherein said staining, soaking or impregnating is by alternating hot and cold thermal baths.

17. The method according to claim 15, wherein said wood is selected from the group consisting of bulk heads, piers, docks, ties, posts, piling, and construction timber.

18. An article of wood treated by the method of claim 15.

19. An antifoulant composition comprising:
   a quaternary ammonium salt;
   a compound selected from the group consisting of 10,10'-oxybisphenoxarsine, phenarsazine oxide, arsanilic acid, roxarsone, methyl arsonic acid, mono methyl arsinic acid, mono sodium methyl arsonate, cacodylic acid and combinations thereof;
   an ultraviolet absorber; and
   at least one member selected from the group consisting of a fungicide, and an antioxidant.

20. The antifoulant composition of claim 19, further comprising said fungicide.

21. The antifoulant composition of claim 20, wherein said fungicide is selected from the group consisting of octyl isothiazalone, 1,2-benzisothiazolin, 5-chloro-2-methyl-4 isothiazolin, 2-methyl-4 isothiazolin, 4,5 dichloro-2-octyl isothiazolin, Triclosan, and combinations thereof.

22. The antifoulant composition of claim 19, further comprising said antioxidant.

23. The antifoulant composition of claim 22, wherein said antioxidant is selected from the group consisting of ethoxyquin, ethoxyquin phosphate, citrate, maleate, propionate, formate, ascorbic acid, ascorbyl palmitate and dipalmitate, ethyl ascorbate, ascorbyl stearate and oleate, tocopherols and tocotrienols, dodecyl and octyl gallate, gallic acid and tannic acid, gamma oryzanol, and thioctic.

24. The antifoulant composition of claim 19, wherein said ultraviolet absorber is selected from the group consisting of titanium dioxide, oxybenzone, benzophenones, bis tetramethyl piperidinyl sebacate, piperidine derivatives or mixtures thereof.

25. The antifoulant composition of claim 1, wherein said quaternary ammonium salt is present in an amount of about 0.05–10 wt. % of the antifoulant composition.

26. An antifoulant composition comprising:
   a compound A selected from the group consisting of denatonium capsaicinate, denatonium saccharide, denatonium chloride, denatonium benzoate, denatonium oleate, denatonium palmitate, benzylalkonium salts, lidocaine, lidocaine HCl, and combinations thereof; and
   a compound B selected from the group consisting of 10,10'-oxybisphenoxarsine, phenarsazine oxide, arsanilic acid, roxarsone, methyl arsonic acid, mono methyl arsinic acid, mono sodium methyl arsonate, cacodylic acid and combinations thereof.

* * * * *